US008492422B2

(12) United States Patent
Dibas et al.

(10) Patent No.: US 8,492,422 B2
(45) Date of Patent: Jul. 23, 2013

(54) ESTER PRO-DRUGS OF [3-(1-(1H-IMIDAZOL-4-YL)ETHYL)-2-METHYLPHENYL] METHANOL FOR TREATING SKIN DISEASES AND CONDITIONS

(75) Inventors: Mohammad I. Dibas, Laguna Niguel, CA (US); Ken Chow, Newport Coast, CA (US); Liming Wang, Irvine, CA (US); Michael E. Garst, Newport Beach, CA (US); John E. Donello, Dana Point, CA (US); Daniel W. Gil, Corona Del Mar, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/233,665

(22) Filed: Sep. 15, 2011

(65) Prior Publication Data
US 2012/0136036 A1 May 31, 2012

Related U.S. Application Data (60) Provisional application No. 61/383,370, filed on Sep. 16, 2010.

(51) Int. Cl.
*A61K 31/4174* (2006.01)
*A61P 17/00* (2006.01)
*C07D 233/64* (2006.01)

(52) U.S. Cl.
USPC ............... 514/400; 548/341.1; 548/339.1; 548/338.1; 548/341.5; 548/346.1

(58) Field of Classification Search
None
See application file for complete search history.

(56) References Cited

U.S. PATENT DOCUMENTS
7,491,383 B2   2/2009   Woodward

FOREIGN PATENT DOCUMENTS
| WO | WO 95-14007 | 5/1995 |
| WO | WO 2005-034998 | 4/2005 |
| WO | WO 2005-115395 | 12/2005 |
| WO | WO 2006-036480 | 4/2006 |
| WO | WO 2009-089132 | 7/2009 |
| WO | WO 2010-091209 | 8/2010 |
| WO | WO 2010093930 | 8/2010 |

OTHER PUBLICATIONS

Culp et al. Pharmacy & Therapeutics 2009, 34 (1), 38-45.*
Shanler et al. Arch. Dermatol. 2007, 143 (11), 1369-1371.*
Cross, L.C. et al., "Rules for the Nomenclature of Organic Chemistry," Pure Appli. Chem., 45, 11-30, 1976.
Patent Cooperation Treaty, Notification of Transmittal of the International Search Report and the Written Opinion of the International Searching Authority, or the Declaration, Form PCT/ISA/220, Int. App. No. PCT/US2011/051979, Oct. 31, 2011.
Stahl, Heinrich & Wermuth, Camille (Eds), Handbook of Pharmaceutical Salts, Verlag Helvetica Chemica Acta- Zürich, 329-345, 2002.
Stella, V. et al., "Pro-drugs as Novel Delivery System", vol. 14 of the A.C.S. Symposium Series "Bioreversible Carriers in Drug Design", ed. Edward B. Roche, American Pharmaceutical Association and Pergamon Press, 1987.
Strasinger, C. et al., "Prodrugs and Codrugs as Strategies for Improving Percutaneous Absorption," Expert Review of Dermatology, vol. 3, No. 2, pp. 221-233, Apr. 1, 2008.
Testa, Bernard et al., "Design of Intramolecularly Activated Prodrugs," Drug Metabolism Reviews, vol. 30, No. 4, 787-807, Jan. 1, 1998.
Hui, Y.-H et al.; "Analytical method development for the simultaneous quantitation of dexmedetomidine and three potential metabolites in plasma"; Journal of Chromatography, (1997), 762(1+2), 281-291.
Stoilov et al.; "Synthesis of detomidine and medetomidine metabolites: 1,2,3-trisubstituted arenes with 4'(5')-imidazolylmethyl groups" in Journal of Heterocyclic Chemistry (1993), 30(6), (1645-1651).
Salonen, et al. "Biotransformation of Medetomidine in the Rat" in Xenobiotica (1990), 20(5), 471-80.
Pierce V. Kavanagh; "Synthesis of Possible Metabolites of Medetomidine {1-(2,3-Dimethylphenyl)-1-[imidazol-4(5)-yl] ethane}"; J. Chem. Research (S), 1993.

* cited by examiner

*Primary Examiner* — Sreeni Padmanabhan
*Assistant Examiner* — Irina Neagu
(74) *Attorney, Agent, or Firm* — Doina G. Ene (57) ABSTRACT

The present invention relates to method for treating skin diseases and skin conditions in a subject in need of such treatment, which comprises administering a therapeutically effective amount of a composition comprising ester pro-drugs of [3-(1-(1H-imidazol-4-yl)ethyl)-2-methylphenyl]methanol, or enantiomers thereof, pharmaceutical compositions containing them and their use as pharmaceuticals.

7 Claims, 2 Drawing Sheets

ESTER PRO-DRUGS OF [3-(1-(1H-IMIDAZOL-4-YL)ETHYL)-2-METHYLPHENYL] METHANOL FOR TREATING SKIN DISEASES AND CONDITIONS

RELATED APPLICATIONS

This application claims priority to U.S. Provisional Patent Application No. 61/383,370 filed on Sep. 16, 2010, the entire disclosure of which is incorporated herein by this reference.

BACKGROUND OF THE INVENTION

1. Field of the Invention

The present invention relates to a method for treating skin diseases and skin conditions in a subject in need of such treatment, which comprises administering a therapeutically effective amount of a composition comprising ester pro-drugs of [3-(1-(1H-imidazol-4-yl)ethyl)-2-methylphenyl]methanol or of its enantiomers.

2. Summary of the Related Art

Three alpha-1 and three alpha-2 adrenergic receptors have been characterized by molecular and pharmacological methods. Activation of these alpha receptors evokes physiological responses with useful therapeutic applications.

Compound, 4-[1-(2,3-dimethylphenyl)ethyl]-3H-imidazole, generically known as, medetomidine is an alpha 2 adrenergic agonist, for use in the sedation of animals. The hydrochloride salt of the (S) enantiomer of medetomidine, generically known as dexmedetomidine, (S) 4-[1-(2,3-dimethylphenyl)ethyl]-3H-imidazole, is also indicated for use as a sedative or analgesic in cats and dogs.

The metabolite of dexmedetomidine is (S)[3-(1-(1H-imidazol-4-yl)ethyl)-2-methylphenyl]methanol together with its racemic mixture, compound [3-(1-(1H-imidazol-4-yl)ethyl)-2-methylphenyl]methanol, are described in the literature in *Journal of Chromatography*, (1997), 762(1+2), 281-291 by Hui, Y.-H et al.

[3-(1-(1H-imidazol-4-yl)ethyl)-2-methylphenyl]methanol is described in "Synthesis of detomidine and medetomidine metabolites: 1,2,3-trisubstituted arenes with 4'(5')-imidazolylmethyl groups" in *Journal of Heterocyclic Chemistry* (1993), 30(6), (1645-1651) by Stoilov et al.

Kavanagh, et al. describe [3-(1-(1H-imidazol-4-yl)ethyl)-2-methylphenyl]methanol in "Synthesis of Possible Metabolites of Medetomidine {1-(2,3-dimethylphenyl)-1-[imidazol-4(5)-yl]ethane" in *Journal of Chemical Research, Synopses* (1993), (4), 152-3.

Medetomidine
4-(1-(2,3-dimethylphenyl)
ethyl)-1H-imidazole
CAS 86347-14-0

Dexmedetomidine
(S)-4-(1-(2,3-dimethylphenyl)
ethyl)-1H-imidazole
CAS 189255-79-6

(3-(1-(1H-imidazol-4-yl)ethyl)-
2-methylphenyl)methanol
CAS 128366-50-7

(R)-(3-(1-(1H-imidazol-4-yl)ethyl)-
2-methylphenyl)methanol
CAS 1240244-32-9

(S)-(3-(1-(1H-imidazol-4-yl)ethyl)-
2-methylphenyl)methanol
CAS 189255-79-6

[3-(1-(1H-imidazol-4-yl)ethyl)-2-methylphenyl)methanol] is described by Salonen, et al. in "Biotransformation of Medetomidine in the Rat" in *Xenobiotica* (1990), 20(5), 471-80.

PCT Int. Appl. WO 2010093930 A1 discloses [3-(1-(1H-imidazol-4-yl)ethyl)-2-methylphenyl]methanol and its (S) and (R) enantiomers.

SUMMARY OF THE RELATED ART

Three alpha 1 and three alpha 2 adrenergic receptors have been characterized by molecular and pharmacological methods. Activation of these alpha 2 receptors evokes physiological responses and has useful therapeutic actions.

The present invention relates to a method for treating skin diseases and skin conditions in a subject in need of such treatment, which comprises administering a therapeutically effective amount of a composition comprising ester pro-drugs of [3-(1-(1H-imidazol-4-yl)ethyl)-2-methylphenyl]methanol. Upon hydrolytic and/or enzymatic cleavage of the ester functionality the parent compound, [3-(1-(1H-imidazol-4-yl)ethyl)-2-methylphenyl]methanol, is released to act as a selective modulator of the alpha 2 adrenergic receptors.

In another aspect, the present invention relates to a method for treating skin diseases and skin conditions in a subject in need of such treatment, which comprises administering a therapeutically effective amount of a composition comprising ester pro-drugs of (S)[3-(1-(1H-imidazol-4-yl)ethyl)-2-methylphenyl]methanol, or pharmaceutical compositions containing them. Upon hydrolytic and/or enzymatic cleavage of the ester functionality the parent compound, active metabolite, (S)[3-(1-(1H-imidazol-4-yl)ethyl)-2-methylphenyl]methanol, is released to act as a selective modulator of the alpha 2 adrenergic receptors.

In another aspect the present invention provides relates to a method for treating skin diseases and skin conditions in a subject in need of such treatment, which comprises administering a therapeutically effective amount of a composition comprising ester pro-drugs of (R)[3-(1-(1H-imidazol-4-yl)ethyl)-2-methylphenyl]methanol, or pharmaceutical compositions containing them. Upon hydrolytic and/or enzymatic cleavage of the ester functionality the parent compound (R)[3-(1-(1H-imidazol-4-yl)ethyl)-2-methylphenyl]methanol, is released to act as a selective modulator of the alpha 2 adrenergic receptors.

The ester pro-drugs of [3-(1-(1H-imidazol-4-yl)ethyl)-2-methylphenyl]methanol will be useful for the treatment or prevention in mammals, including humans, of a range of skin diseases and skin conditions which include, but are not limited to: rosacea, sunburn, chronic sun damage, discreet erythemas, psoriasis, atopic dermatitis, menopause-associated hot flashes, hot flashes resulting from orchiectomyatopic dermatitis, photoaging, seborrheic dermatitis, acne, allergic dermatitis, irritant dermatitis, telangiectasia (dilations of previously existing small blood vessels) of the face, rhinophyma (hypertrophy of the nose with follicular dilation), red bulbous nose, acne-like skin eruptions (may ooze or crust), burning or stinging sensation of the face, irritated and bloodshot and watery eyes, cutaneous hyperactivity with dilation of blood vessels of the skin, Lyell's syndrome, Stevens-Johnson syndrome, erythema multiforme minor, erythema multiforme major and other inflammatory skin diseases. Skin conditions which result in rosacea can be induced by intake of spicy food, of alcohol, of chocolate, of hot or alcoholic drinks, temperature variations, heat, exposure to ultraviolet or infrared radiation, exposure to low relative humidity, exposure of the skin to strong winds or currents of air, exposure of the skin to surfactants, irritants, irritant dermatological topical agents, and cosmetics.

DETAILED DESCRIPTION OF THE INVENTION

The present invention relates to a method for treating skin diseases and skin conditions in a subject in need of such treatment, which comprises administering a therapeutically effective amount of a composition comprising ester pro-drugs of [3-(1-(1H-imidazol-4-yl)ethyl)-2-methylphenyl]methanol, ester pro-drugs of (S)[3-(1-(1H-imidazol-4-yl)ethyl)-2-methylphenyl]methanol and ester pro-drugs of (R)[3-(1-(1H-imidazol-4-yl)ethyl)-2-methylphenyl]methanol or the tautomers thereof, or pharmaceutically acceptable salts thereof.

The term "subject", as used herein, refers to a human patient.

In a preferred embodiment the present invention relates to a method for treating skin diseases and skin conditions in a subject in need of such treatment, which comprises administering a therapeutically effective amount of a composition comprising esters pro-drugs of (S)-[3-(1-(1H-imidazol-4-yl)ethyl)-2-methylphenyl]methanol or the tautomers thereof, or pharmaceutically acceptable salts thereof. Upon hydrolytic or enzymatic cleavage of the ester functionality the parent compound, active metabolite, (S)-[3-(1-(1H-imidazol-4-yl)ethyl)-2-methylphenyl]methanol, is released to act as a selective modulator of the alpha 2 adrenergic receptors.

In one aspect of the invention, there is provided a method for treating skin diseases and skin conditions in a patient in need thereof which comprises, consists essentially of or consists of administering a therapeutically effective amount of a pharmaceutical composition comprising, consisting essentially of or consisting of a therapeutically effective amount of ester pro-drugs of [3-(1-(1H-imidazol-4-yl)ethyl)-2-methylphenyl]methanol, or the tautomers thereof, or pharmaceutically acceptable salts thereof.

In another aspect of the invention, there is provided a method for treating skin diseases and skin conditions in a patient in need thereof which comprises, consists essentially of or consists of administering a therapeutically effective amount of a pharmaceutical composition comprising, consisting essentially of or consisting of a therapeutically effective amount of ester pro-drugs (S)[3-(1-(1H-imidazol-4-yl)ethyl)-2-methylphenyl]methanol, or the tautomers thereof, or pharmaceutically acceptable salts thereof.

In another aspect of the invention, there is provided a method for treating skin diseases and skin conditions in a patient in need thereof which comprises, consists essentially of or consists of administering a therapeutically effective amount of a pharmaceutical composition comprising, consisting essentially of or consisting of a therapeutically effective amount of ester pro-drugs of (R)[3-(1-(1H-imidazol-4-yl)ethyl)-2-methylphenyl]methanol, or the tautomers thereof, or pharmaceutically acceptable salts thereof.

In another aspect of the invention, there is provided a method for treating or improving skin diseases and skin conditions including but not limited to: rosacea, sunburn, chronic sun damage, discreet erythemas, psoriasis, atopic dermatitis, menopause-associated hot flashes, hot flashes resulting from orchiectomyatopic dermatitis, photoaging, seborrheic dermatitis, acne, allergic dermatitis, irritant dermatitis, telangiectasia (dilations of previously existing small blood vessels) of the face, rhinophyma (hypertrophy of the nose with follicular dilation), red bulbous nose, acne-like skin eruptions (may ooze or crust), burning or stinging sensation of the face, irritated and bloodshot and watery eyes, cutaneous hyperactivity with dilation of blood vessels of the skin, Lyell's syndrome, Stevens-Johnson syndrome, erythema multiforme minor, erythema multiforme major and other inflammatory skin diseases. Skin conditions which result in rosacea can be induced by intake of spicy food, of alcohol, of chocolate, of hot or alcoholic drinks, temperature variations, heat, exposure to ultraviolet or infrared radiation, exposure to low relative humidity, exposure of the skin to strong winds or currents of air, exposure of the skin to surfactants, irritants, irritant dermatological topical agents, and cosmetics.

In another aspect of the invention, there is provided a method for treating or improving skin diseases and skin conditions including but not limited to: rosacea, sunburn, chronic sun damage, discreet erythemas, psoriasis, atopic dermatitis, menopause-associated hot flashes, hot flashes resulting from orchiectomyatopic dermatitis, photoaging, seborrheic dermatitis, acne, allergic dermatitis, irritant dermatitis, telangiectasia (dilations of previously existing small blood vessels) of the face, rhinophyma (hypertrophy of the nose with follicular dilation), red bulbous nose, acne-like skin eruptions (may ooze or crust), burning or stinging sensation of the face, irritated and bloodshot and watery eyes, cutaneous hyperactivity with dilation of blood vessels of the skin, Lyell's syndrome, Stevens-Johnson syndrome, erythema multiforme minor, erythema multiforme major and or other inflammatory skin diseases, which comprises, consists essentially of or consists of administering a therapeutically effective amount of a pharmaceutical composition comprising, consisting essentially of or consisting of a therapeutically effective amount of ester pro-drugs of [3-(1-(1H-imidazol-4-yl)ethyl)-2-methylphenyl]methanol, or the tautomers thereof, or pharmaceutically acceptable salts thereof.

In another aspect of the invention, there is provided a method for treating or improving skin diseases and skin conditions including but not limited to: rosacea, sunburn, chronic sun damage, discreet erythemas, psoriasis, atopic dermatitis, menopause-associated hot flashes, hot flashes resulting from orchiectomyatopic dermatitis, photoaging, seborrheic dermatitis, acne, allergic dermatitis, irritant dermatitis, telangiectasia (dilations of previously existing small blood vessels) of the face, rhinophyma (hypertrophy of the nose with follicular dilation), red bulbous nose, acne-like skin eruptions (may ooze or crust), burning or stinging sensation of the face, irritated and bloodshot and watery eyes, cutaneous hyperactivity with dilation of blood vessels of the skin, Lyell's syndrome, Stevens-Johnson syndrome, erythema multiforme minor, erythema multiforme major and or other inflammatory skin diseases, which comprises, consists essentially of or consists of administering a therapeutically effective amount of a pharmaceutical composition comprising, consisting essentially of or consisting of a therapeutically effective amount of ester pro-drugs of (S)[3-(1-(1H-imidazol-4-yl)ethyl)-2-methylphenyl]methanol, or the tautomers thereof, or pharmaceutically acceptable salts thereof.

In another aspect of the invention, there is provided a method for treating or improving skin diseases and skin conditions including but not limited to: rosacea, sunburn, chronic sun damage, discreet erythemas, psoriasis, atopic dermatitis, menopause-associated hot flashes, hot flashes resulting from orchiectomyatopic dermatitis, photoaging, seborrheic dermatitis, acne, allergic dermatitis, irritant dermatitis, telangiectasia (dilations of previously existing small blood vessels) of the face, rhinophyma (hypertrophy of the nose with follicular dilation), red bulbous nose, acne-like skin eruptions (may ooze or crust), burning or stinging sensation of the face, irritated and bloodshot and watery eyes, cutaneous hyperactivity with dilation of blood vessels of the skin, Lyell's syndrome, Stevens-Johnson syndrome, erythema multiforme minor, erythema multiforme major and or other inflammatory skin diseases, which comprises, consists essentially of or consists of administering a therapeutically effective amount of a pharmaceutical composition comprising, consisting essentially of or consisting of a therapeutically effective amount of ester pro-drugs of (R)[3-(1-(1H-imidazol-4-yl)ethyl)-2-methylphenyl]methanol, or the tautomers thereof, or pharmaceutically acceptable salts thereof.

In another aspect of the invention, there is provided a method for treating skin diseases and conditions including but not limited to rosacea induced by intake of spicy food, of chocolate, of alcohol, of hot or alcoholic drinks, temperature variations, heat, exposure to ultraviolet or infrared radiation, exposure to low relative humidity, exposure of the skin to strong winds or currents of air, exposure of the skin to surfactants, irritants, irritant dermatological topical agents, and cosmetics.

In another aspect of the invention, there is provided a method for treating skin diseases and conditions including but not limited to rosacea induced by intake of spicy food, of chocolate, of alcohol, of hot or alcoholic drinks, temperature variations, heat, exposure to ultraviolet or infrared radiation, exposure to low relative humidity, exposure of the skin to strong winds or currents of air, exposure of the skin to surfactants, irritants, irritant dermatological topical agents, and cosmetics, which comprises, consists essentially of or consists of or consists of administering a therapeutically effective amount of a pharmaceutical composition comprising, consisting essentially of or consisting of a therapeutically effective amount of ester pro-drugs of [3-(1-(1H-imidazol-4-yl)ethyl)-2-methylphenyl]methanol, or the tautomers thereof, or pharmaceutically acceptable salts thereof.

In another aspect of the invention, there is provided a method for treating skin diseases and conditions including but not limited to rosacea induced by intake of spicy food, of chocolate, of alcohol, of hot or alcoholic drinks, temperature variations, heat, exposure to ultraviolet or infrared radiation, exposure to low relative humidity, exposure of the skin to strong winds or currents of air, exposure of the skin to surfactants, irritants, irritant dermatological topical agents, and cosmetics, which comprises, consists essentially of or consists of or consists of administering a therapeutically effective amount of a pharmaceutical composition comprising, consisting essentially of or consisting of a therapeutically effective amount of ester pro-drugs of (S)[3-(1-(1H-imidazol-4-yl)ethyl)-2-methylphenyl]methanol, or the tautomers thereof, or pharmaceutically acceptable salts thereof.

In another aspect of the invention, there is provided a method for treating skin diseases and conditions including but not limited to rosacea induced by intake of spicy food, of chocolate, of alcohol, of hot or alcoholic drinks, temperature variations, heat, exposure to ultraviolet or infrared radiation, exposure to low relative humidity, exposure of the skin to strong winds or currents of air, exposure of the skin to surfactants, irritants, irritant dermatological topical agents, and cosmetics, which comprises, consists essentially of or consists of or consists of administering a therapeutically effective amount of a pharmaceutical composition comprising, consisting essentially of or consisting of a therapeutically effective amount of ester pro-drugs of (R)[3-(1-(1H-imidazol-4-yl)ethyl)-2-methylphenyl]methanol, or the tautomers thereof, or pharmaceutically acceptable salts thereof.

In another aspect of the invention, there is provided a method for treating skin diseases and skin conditions wherein the pharmaceutical composition comprising, consisting essentially of or consisting of a therapeutically effective amount ester pro-drugs of [3-(1-(1H-imidazol-4-yl)ethyl)-2-methylphenyl]methanol, is selected from topical skin application, direct injection, applications and formulations that may further enhance the long duration of actions such as a slow releasing pellet, suspension, gel, solution, cream, lotion, ointment, foams, emulsions, microemulsions, milks, serums, aerosols, sprays, dispersions, microcapsules, vesicles, microparticles, nanoparticles, wet cloths, dry cloths, facial cloths.

In another aspect of the invention, there is provided a method for treating skin diseases and skin conditions wherein the pharmaceutical composition comprising, consisting essentially of or consisting of a therapeutically effective amount of ester pro-drugs of (S)[3-(1-(1H-imidazol-4-yl)ethyl)-2-methylphenyl]methanol is selected from topical skin application, direct injection, applications and formulations that may further enhance the long duration of actions such as a slow releasing pellet, suspension, gel, solution, cream, lotion, ointment, foams, emulsions, microemulsions, milks, serums, aerosols, sprays, dispersions, microcapsules, vesicles, microparticles, nanoparticles, wet cloths, dry cloths, facial cloths.

In another aspect of the invention, there is provided a method for treating skin diseases and skin conditions wherein the pharmaceutical composition comprising, consisting essentially of or consisting of a therapeutically effective amount of ester pro-drugs of (R)[3-(1-(1H-imidazol-4-yl)ethyl)-2-methylphenyl]methanol is selected from topical skin application, direct injection, applications and formulations that may further enhance the long duration of actions such as a slow releasing pellet, suspension, gel, solution, lotion, cream, ointment, foams, emulsions, microemulsions, milks, serums, aerosols, sprays, dispersions, microcapsules, vesicles, microparticles, nanoparticles, wet cloths, soaps, cleansing bars, dry cloths, facial cloths.

In another aspect of the invention, there is provided a method of decreasing the irritation of skin associated with rosacea treatment regimen of topically applied a therapeutically effective amount of ester pro-drugs of [3-(1-(1H-imidazol-4-yl)ethyl)-2-methylphenyl]methanol, of (S)[3-(1-(1H-imidazol-4-yl)ethyl)-2-methylphenyl]methanol or of (R)[3-(1-(1H-imidazol-4-yl)ethyl)-2-methylphenyl]methanol, the method of treating telangiectasia with a therapeutically effective amount of ester pro-drugs of [3-(1-(1H-imidazol-4-yl)ethyl)-2-methylphenyl]methanol, of (S)[3-(1-(1H-imidazol-4-yl)ethyl)-2-methylphenyl]methanol or of (R)[3-(1-(1H-imidazol-4-yl)ethyl)-2-methylphenyl]methanol and therefore, it also includes the method of reducing redness associated with the appearance of rosacea.

The present invention is beneficial when used in conjunction with topically applied or oral rosacea treatments of such as retinoids (isotretinoin), metronidazole, tertracyclines (doxycycline), phytosphingosine, antibacterial agents, antiparasitic agents, antifungal agents, anti-inflammatory agents, antihistamines, anti-pruriginous agents, anesthetics, antiviral agents, keratolytic agents, anti free-radical agents, anti seborrheic agents, antidandruff agents, anti acne agents, sunscreens and sun blocking agents, and active agents which modify at least one of cutaneous differentiation, proliferation, and pigmentation.

The present invention is beneficial when used in conjunction with topically applied or oral rosacea treatments such as retinoids (isotretinoin), metronidazole, tertracyclines (doxycycline), phytoshingosine, antibacterial agents, antiparasitic agents, antifungal agents, anti-inflammatory agents, antihistamines, anti-pruriginous agents, anesthetics, antiviral agents, keratolytic agents, anti free-radical agents, anti seborrheic agents, antidandruff agents, anti acne agents, sunscreens and sun blocking agents, and active agents which modify at least one of cutaneous differentiation, proliferation, and pigmentation, which comprises, consists essentially of or consists of or consists of administering a therapeutically effective amount of a pharmaceutical composition comprising, consisting essentially of or consisting of a therapeutically effective amount of ester pro-drugs of [3-(1-(1H-imidazol-4-yl)ethyl)-2-methylphenyl]methanol, or the tautomers thereof, or pharmaceutically acceptable salts thereof.

The present invention is beneficial when used in conjunction with topically applied or oral rosacea treatments of such as retinoids (isotretinoin), metronidazole, tertracyclines (doxycycline), phytosphingosine, antibacterial agents, antiparasitic agents, antifungal agents, anti-inflammatory agents, antihistamines, anti-pruriginous agents, anesthetics, antiviral agents, keratolytic agents, anti free-radical agents, anti seborrheic agents, antidandruff agents, anti acne agents, sunscreens and sun blocking agents, and active agents which modify at least one of cutaneous differentiation, proliferation, and pigmentation, which comprises, consists essentially of or consists of or consists of administering a therapeutically effective amount of a pharmaceutical composition comprising, consisting essentially of or consisting of a therapeutically effective amount of ester pro-drugs of (S)[3-(1-(1H-imidazol-4-yl)ethyl)-2-methylphenyl]methanol, or the tautomers thereof, or pharmaceutically acceptable salts thereof.

The present invention is beneficial when used in conjunction with topically applied or oral rosacea treatments of such as retinoids (isotretinoin), metronidazole, tertracyclines (doxycycline), phytosphingosine, antibacterial agents, antiparasitic agents, antifungal agents, anti-inflammatory agents, antihistamines, anti-pruriginous agents, anesthetics, antiviral agents, keratolytic agents, anti free-radical agents, anti seborrheic agents, antidandruff agents, anti acne agents, sunscreens and sun blocking agents, and active agents which modify at least one of cutaneous differentiation, proliferation, and pigmentation, which comprises, consists essentially of or consists of or consists of administering a therapeutically effective amount of a pharmaceutical composition comprising, consisting essentially of or consisting of a therapeutically effective amount of ester pro-drugs of (R)[3-(1-(1H-imidazol-4-yl)ethyl)-2-methylphenyl]methanol, or the tautomers thereof, or pharmaceutically acceptable salts thereof.

"Prodrugs" are frequently referred to by the term "metabolically cleavable derivatives" which refers to compound forms which are rapidly transformed in vivo to the parent compound according to the invention, for example, by hydrolysis in blood. Thus, prodrugs are compounds bearing groups which are removed by biotransformation prior to exhibiting their pharmacological action. Such groups include moieties which are readily cleaved in vivo from the compound bearing it, which compound after cleavage remains or becomes pharmacologically active. Such metabolically cleavable groups form a class well known to practitioners of the art. They include, but are not limited to such groups as alkanoyl (i.e. acetyl, propionyl, butyryl, and the like), unsubstituted and substituted carbocyclic aroyl (such as benzoyl, substituted benzoyl and 1- and 2-naphthoyl), alkoxycarbonyl (such as ethoxycarbonyl), trialklysilyl (such as trimethyl- and triethylsilyl), monoesters formed with dicarboxylic acids (such as succinyl), phosphate, sulfate, sulfonate, sulfonyl, sulfinyl and the like. The compounds bearing the metabolically cleavable groups have the advantage that they may exhibit improved bioavailability as a result of enhanced solubility and/or rate of absorption conferred upon the parent compound by virtue of the presence of the metabolically cleavable group. (T. Higuchi and V. Stella, "Pro-drugs as Novel Delivery System", Vol. 14 of the A.C.S. Symposium Series; "Bioreversible Carriers in Drug Design", ed. Edward B. Roche, American Pharmaceutical Association and Pergamon Press, 1987).

In one aspect, the invention therefore relates to a method for treating skin diseases and skin conditions in a subject in need of such treatment, which comprises administering a therapeutically effective amount of a composition comprising a compound having Formula I, its individual enantiomers, its individual diastereoisomers, its individual hydrates, its individual solvates, its individual crystal forms, its individual isomers, its individual tautomers or a pharmaceutically acceptable salt thereof, Formula I wherein
$R^1$ is H or $C_{1-3}$ alkyl;
$R^2$ is H or $C_{1-3}$ alkyl;
$R^3$ is H, $C_{1-10}$ alkyl, heterocycle or aryl; and
R is $C_{1-10}$ alkyl, heterocycle or aryl.

In a preferred aspect, the invention therefore relates to a method for treating skin diseases and skin conditions in a subject in need of such treatment, which comprises administering a therapeutically effective amount of a composition comprising a compound having Formula II, its individual diastereoisomers, its individual hydrates, its individual solvates, its individual crystal forms, its individual isomers, its individual tautomers or a pharmaceutically acceptable salt thereof, Formula II wherein
$R^1$ is H or $C_{1-3}$ alkyl;
$R^2$ is H or $C_{1-3}$ alkyl;
$R^3$ is H, $C_{1-10}$ alkyl, heterocycle or aryl; and
R is $C_{1-10}$ alkyl, heterocycle or aryl.

In another aspect, the invention therefore relates to a method for treating skin diseases and skin conditions in a subject in need of such treatment, which comprises administering a therapeutically effective amount of a composition comprising a compound having Formula III, its individual diastereoisomers, its individual hydrates, its individual solvates, its individual crystal forms, its individual isomers, its individual tautomers or a pharmaceutically acceptable salt thereof, Formula III wherein
$R^1$ is H or $C_{1-3}$ alkyl;
$R^2$ is H or $C_{1-3}$ alkyl;
$R^3$ is H, $C_{1-10}$ alkyl, heterocycle or aryl; and
R is $C_{1-10}$ alkyl, heterocycle or aryl.

In another aspect, the present invention relates to pharmaceutical compositions containing as active ingredient ester pro-drugs of [3-(1-(1H-imidazol-4-yl)ethyl)-2-methylphenyl]methanol for treatment of skin diseases and skin conditions.

In another aspect, the present invention relates to pharmaceutical compositions containing as active ingredient ester pro-drugs (S)[3-(1-(1H-imidazol-4-yl)ethyl)-2-methylphenyl]methanol for treatment of skin diseases and skin conditions.

In another aspect, the present invention relates to pharmaceutical compositions containing as active ingredient ester pro-drugs of (R)[3-(1-(1H-imidazol-4-yl)ethyl)-2-methylphenyl]methanol for treatment of skin diseases and skin conditions.

The following paragraphs provide definitions of the various chemical moieties that make up the compounds of the invention and are intended to apply uniformly throughout the specification and claims unless expressly stated otherwise.

The term "alkyl" as used herein, is defined as including a saturated monovalent alkane moiety having straight or branched alkane moieties or combinations thereof and containing 1-10 carbon atoms, preferably 1-8 carbon atoms and more preferably 1-4 carbon atoms. Alkyl moieties can optionally be substituted by, but not limited to, amino groups, aryl groups, halogens. One methylene (—$CH_2$—) of the alkyl chain, can be replaced by carbonyl, —NH—, carboxyl, amide, sulfur or by oxygen. Examples include, but are not limited to, methyl, ethyl, propyl, butyl, sec-butyl, pentyl, iso-pentyl, neo-pentyl, hexyl, iso-hexyl, 3-methyl-butyl, 2-amino-N-isobutyl acetamide, iso-butyl, tert-butyl, iso-propyl, ethylphenyl, methylphenyl, 2-amino-3-methyl-butanamide-N-2-methyl-1-propyl, 1-amino-2-methyl-prop-1-yl.

The term "heterocycle" as used herein is defined as an aromatic or non aromatic 5 to 10 membered monocyclic or bicyclic ring containing at least one heteroatom selected from O or N or S or combinations thereof, interrupting the carbocyclic ring structure. Heterocycles can optionally be substituted by, but not limited to, $C_{1-6}$ alkyl, amino, halogen, —O($C_{1-6}$ alkyl), —OC(O)($C_{1-6}$ alkyl), —C(O)O($C_{1-6}$ alkyl), —NHC(O)($C_{1-6}$ alkyl), —C(O)NH($C_{1-6}$ alkyl), —S($C_{1-6}$ alkyl) groups. Examples include, but are not limited to, furyl, pyrryl, pyridyl, pyrimidyl, thienyl, isothiazolyl, imidazolyl, pyrazinyl, benzofuranyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,5-thiadiazolyl, 1,2,4-thiadiazolyl, isooxazolyl, quinazolinyl, pyridazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, pyrrolidinyl, piperidinyl and piperazinyl.

The term "aryl" as used herein, is defined as including an organic moiety derived from an aromatic hydrocarbon consisting of a monocyclic or bicyclic ring containing 6-10 carbon atoms by removal of one hydrogen atom, such as phenyl or naphtyl. Aryl groups can optionally be substituted by, but not limited to, $C_{1-6}$ alkyl, amino, halogen, —O($C_{1-6}$ alkyl), —OC(O)($C_{1-6}$ alkyl), —C(O)O($C_{1-6}$ alkyl), —NHC(O)($C_{1-6}$ alkyl), —C(O)NH($C_{1-6}$ alkyl), —S($C_{1-6}$ alkyl) groups. Examples include, but are not limited to, phenyl, naphtyl.

The term "H" as used herein refers to a hydrogen atom.
The term "O" as used herein refers to an oxygen atom.
The term "S" as used herein refers to a sulfur atom.
The term "N" as used herein refers to a nitrogen atom.
The term "amino" as used herein refers to a group of formula —$NH_2$.
The term "amide" as used herein refers to a group of formula —C(O)NH— or —NHC(O)—.

The term "halogen", as used herein refers to an atom of chlorine, bromine, iodine or fluorine.

The term "carbonyl" as used herein refers to a group of formula —C=O.

The term "carboxyl", as used herein refers to a group of formula —C(O)O— or —OC(O)—.

Generally $R^1$ is H or $C_{1-3}$ alkyl. Preferred $R^1$ is $C_{1-3}$ alkyl. Most preferred $R^1$ is methyl.

Generally $R^2$ is H or $C_{1-3}$ alkyl. Preferred $R^2$ is $C_{1-3}$ alkyl. Most preferred $R^2$ is methyl.

Generally $R^3$ is H, $C_{1-10}$ alkyl, heterocycle or aryl. Preferred $R^3$ is H, phenyl or $C_{1-10}$ alkyl. Most preferred $R^3$ is H.

Generally R is $C_{1-10}$ alkyl, heterocycle or aryl. Preferred R is methyl, iso-butyl, tert-butyl, iso-propyl, ethylphenyl, phenyl, 2-amino-1-phenylethyl, 2-(2-amino-3-methyl-butyrylamino)-2-methyl-prop-1-yl, 1-amino-2-methyl-prop-1-yl, 2-(2-amino-acetylamino)-2-methyl-prop-1-yl. Most preferred R groups are tert-butyl, iso-propyl.

As used herein, "tautomer" refers to the migration of protons between adjacent single and double bonds. The tautomerization process is reversible. Compounds described herein can undergo any possible tautomerization that is within the physical characteristics of the compound. The following is a tautomerization example that can occur in compounds described herein:

Compounds of the invention are:
iso-Butyric acid 3-[(S)-1-(1H-imidazol-4-yl)ethyl]-2-methyl-benzyl ester;
2,2-Dimethyl-propionic acid 3-[(S)-1-(1H-imidazol-4-yl)ethyl]-2-methyl-benzyl ester;
Acetic acid 3-[(S)-1-(1H-imidazol-4-yl)ethyl]-2-methyl-benzyl ester;
Benzoic acid 3-[(S)-1-(1H-imidazol-4-yl)-ethyl]-2-methyl-benzyl ester;
3-Methyl-butyric acid 3-[(S)-1-(1H-imidazol-4-yl)-ethyl]-2-methyl-benzyl ester;
3-Phenyl-propionic acid 3-[(S)-1-(1H-imidazol-4-yl)-ethyl]-2-methyl-benzyl ester;
2-Amino-3-methyl-butyric acid 3-[(S)-1-(1H-imidazol-4-yl)-ethyl]-2-methyl-benzyl ester;
2-(2-Amino-3-methyl-butyrylamino)-3-methyl-butyric acid 3-[(S)-1-(1H-imidazol-4-yl)-ethyl]-2-methyl-benzyl ester;
2-(2-Amino-acetylamino)-3-methyl-butyric acid 3-[(S)-1-(1H-imidazol-4-yl)-ethyl]-2-methyl-benzyl ester;
2-Amino-3-phenyl-propionic acid 3-[(S)-1-(1H-imidazol-4-yl)-ethyl]-2-methyl-benzyl ester.

Intermediates of the invention are:
iso-Butyric acid 3-[(S)-1-(1-iso-butyryl-1H-imidazol-4-yl)-ethyl]-2-methyl-benzyl ester;
2,2-Dimethyl-propionic acid 3-{(S)-1-[1-(2,2-dimethyl-propionyl)-1H-imidazol-4-yl]-ethyl}-2-methyl-benzyl ester;
Acetic acid 3-[(S)-1-(1-acetyl-1H-imidazol-4-yl)-ethyl]-2-methyl-benzyl ester;
Benzoic acid 3-[(S)-1-(1-benzoyl-1H-imidazol-4-yl)-ethyl]-2-methyl-benzyl ester;
3-Methyl-butyric acid 2-methyl-3-{(S)-1-[1-(3-methyl-butyryl)-1H-imidazol-4-yl]-ethyl}-benzyl ester;
Phenyl-propionic acid 2-methyl-3-{(S)-1-[1-(3-phenyl-propionyl)-1H-imidazol-4-yl]-ethyl}-benzyl ester;
2-tert-Butoxycarbonylamino-3-methyl-butyric acid 3-{(S)-1-[1-(2-tert-butoxy carbonylamino-3-methyl-butyryl)-1H-imidazol-4-yl]-ethyl}-2-methyl-benzyl ester;
2-tert-Butoxycarbonylamino-3-methyl-butyric acid 3-[(S)-1-(1H-imidazol-4-yl)-ethyl]-2-methyl-benzyl ester;
2-(2-tert-Butoxycarbonylamino-3-methyl-butyrylamino)-3-methyl-butyric acid 3-{(S)-1-[1-(2-tert-butoxycarbonylamino-3-methyl-butyryl)-1H-imidazol-4-yl]-ethyl}-2-methyl-benzyl ester;
2-(2-tert-Butoxycarbonylamino-3-methyl-butyrylamino)-3-methyl-butyric acid 3-[(S)-1-(1H-imidazol-4-yl)-ethyl]-2-methyl-benzyl ester;
2-(2-tert-Butoxycarbonylamino-acetylamino)-3-methyl-butyric acid 3-[(S)-1-(1H-imidazol-4-yl)-ethyl]-2-methyl-benzyl ester;
2-tert-Butoxycarbonylamino-3-phenyl-propionic acid 3-[(S)-1-(1H-imidazol-4-yl)-ethyl]-2-methyl-benzyl ester.

Some compounds of Formula I, Formula II and Formula III and some of their intermediates have at least one stereogenic center in their structure. This stereogenic center may be present in an (R) or (S) configuration, said (R) and (S) notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I, Formula II or Formula III are able to form.

The acid addition salt form of a compound of Formula I, Formula II or Formula III that occurs in its free form as a base can be obtained by treating the free base with an appropriate acid such as an inorganic acid, for example but not limited to, hydrochloric acid, hydrobromic acid, sulfuric acid, phosphoric acid, nitric acid and the like; or an organic acid such as for example but not limited to, as citric acid, acetic acid, oxalic acid, tartaric acid, succinic acid, malic acid, fumaric acid, ascorbic acid, benzoic acid, tannic acid, palmoic acid, alginic acid, polyglutamic acid, naphthalene-sulfonic acid, napthalenedisulfonic, and polygalacturonic acid as well as base addition salts such as those formed with alkali- and alkaline earth metals such as sodium, potassium and calcium and the like (Handbook of Pharmaceutical Salts, P. Heinrich Stahal & Camille G. Wermuth (Eds), Verlag Helvetica Chemica Acta-Zürich, 2002, 329-345).

The compounds can also be administered as pharmaceutically acceptable quaternary salts known by those skilled in the art, which specifically include, but not limiting to the quaternary ammonium salt of the formula —$NY^+Z^-$, wherein Y is hydrogen, alkyl, or benzyl, and Z is a counterion, including but not limited to, chloride, bromide, iodide, —O-alkyl, toluenesulfonate, methylsulfonate, sulfonate, phosphate, or carboxylate (such as fumarate, benzoate, succinate, acetate, glycolate, maleate, malate, fumarate, citrate, tartrate, ascorbate, benzoate, cinnamoate, mandeloate, benzyloate, and diphenylacetate).

In another embodiment of the invention, there are provided pharmaceutical compositions including at least one compound of the invention in a pharmaceutically acceptable carrier thereof. The phrase "pharmaceutically acceptable"

means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include but are not limited to, glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

The present invention concerns also the use of a compound of Formula I, Formula II or Formula III, or a pharmaceutically acceptable salt thereof, for the manufacture of a medicament for the therapeutic application. The present invention concerns also the a method for manufacturing a medicament intended for therapeutic application wherein a compound having general Formula I, Formula II or Formula III, or a pharmaceutically active derivative or salt thereof is used.

Since individual subjects may present a wide variation in severity of symptoms and each drug has its unique therapeutic characteristics, the precise mode of administration and dosage employed for each subject is left to the discretion of the practitioner. The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. The actual amount of the compound to be administered in any given case will be determined by a physician taking into account the relevant circumstances, such as the severity of the condition, the age and weight of the patient, the patient's general physical condition, the cause of the condition, and the route of administration. Additionally, the formulations may be designed to delay release of the active compound over a given period of time, or to carefully control the amount of drug released at a given time during the course of therapy.

Ester pro-drugs of [3-(1-(1H-imidazol-4-yl)ethyl)-2-methylphenyl]methanol, of (S)[3-(1-(1H-imidazol-4-yl)ethyl)-2-methylphenyl]methanol or of (R)[3-(1-(1H-imidazol-4-yl)ethyl)-2-methylphenyl]methanol and their pharmaceutically-acceptable salts have extended alpha-2 adrenergic receptor agonist activity in treating skin diseases and skin conditions and may be administered through different routes, including but not limited to topical skin patches, direct injection, formulations that may further enhance the long duration of actions such as a slow releasing pellet, suspension, gel, or sustained delivery devices such as any suitable drug delivery system (DDS) known in the art.

Skin diseases and skin conditions which may be treated with pharmaceutical compositions containing as active ingredient ester pro-drugs of [3-(1-(1H-imidazol-4-yl)ethyl)-2-methylphenyl]methanol, of (S)[3-(1-(1H-imidazol-4-yl)ethyl)-2-methylphenyl]methanol or of (R)[3-(1-(1H-imidazol-4-yl)ethyl)-2-methylphenyl]methanol include, but are not limited to: rosacea, sunburn, chronic sun damage, discreet erythemas, psoriasis, atopic dermatitis, menopause-associated hot flashes, hot flashes resulting from orchiecto-myatopic dermatitis, photoaging, seborrheic dermatitis, acne, allergic dermatitis, irritant dermatitis, telangiectasia (dilations of previously existing small blood vessels) of the face, rhinophyma (hypertrophy of the nose with follicular dilation), red bulbous nose, acne-like skin eruptions (may ooze or crust), burning or stinging sensation of the face, irritated and bloodshot and watery eyes, cutaneous hyperactivity with dilation of blood vessels of the skin, Lyell's syndrome, Stevens-Johnson syndrome, erythema multiforme minor, erythema multiforme major and or other inflammatory skin diseases and other inflammatory skin diseases. Skin conditions which result in rosacea can be induced by intake of spicy food, of alcohol, of chocolate, of hot or alcoholic drinks, temperature variations, heat, exposure to ultraviolet or infrared radiation, exposure to low relative humidity, exposure of the skin to strong winds or currents of air, exposure of the skin to surfactants, irritants, irritant dermatological topical agents, and cosmetics.

"Pharmaceutical composition," as used here, means a composition that is suitable for administering to human patients for the treatment of disease. In one embodiment, therefore, the compound of the invention is formulated as pharmaceutically acceptable salts and further include one or more pharmaceutically acceptable excipients.

Ester pro-drugs of [3-(1-(1H-imidazol-4-yl)ethyl)-2-methylphenyl]methanol, of (S)[3-(1-(1H-imidazol-4-yl)ethyl)-2-methylphenyl]methanol or of (R)[3-(1-(1H-imidazol-4-yl)ethyl)-2-methylphenyl]methanol may be formulated with efficacy enhancing components as disclosed in U.S. Pat. No. 7,491,383 B2, which is hereby incorporated by reference in its entirety.

The ester pro-drugs of [3-(1-(1H-imidazol-4-yl)ethyl)-2-methylphenyl]methanol, of (S)[3-(1-(1H-imidazol-4-yl)ethyl)-2-methylphenyl]methanol or of (R)[3-(1-(1H-imidazol-4-yl)ethyl)-2-methylphenyl]methanol have physiochemical and pharmacokinetic properties that are beneficial for sustained activity, particularly when the drug is delivered continuously (e.g. to the skin by a dermal patch).

The compounds may be administered through different routes, including but not limited to topical dermatological application of an effective dose, direct injection, or formulations that may further enhance the long duration of actions such as a slow releasing pellet, suspension, gel, solution, lotion, cream, ointment, foams, emulsions, microemulsions, milks, serums, aerosols, sprays, dispersions, microcapsules, vesicles, microparticles, nanoparticles, wet cloths, dry cloths, facial cloths.

With respect to the present invention reference to a compound or compounds, is intended to encompass that compound in each of its possible isomeric forms and mixtures thereof unless the particular isomeric form is referred to specifically.

The present invention also concerns a process for preparing the compounds having general Formula I, Formula II or Formula III. The synthetic scheme set forth below, illustrates how compounds according to the invention can be made. Those skilled in the art will be able to routinely modify and/or adapt the following scheme to synthesize any compounds of the invention covered by Formula I, Formula II or Formula III.

General Scheme for Synthesizing Ester Prodrugs of (S)-[3-(1-(1H-imidazol-4-yl)ethyl)-2-methylphenyl] methanol (S)-(3-(1-(1H-imidazol-4-yl)ethyl)-2-methylphenyl)methanol intermediate $R^3$ is H In a first step (S)-[3-(1-(1H-imidazol-4-yl)ethyl)-2-methylphenyl]methanol (CAS 189255-79-6) can react with the desired acyl chloride, in the presence of N,N-dimethyl formamide (DMF), tertahydrofuran (THF), triethylamine (TEA) and 4-dimethyl aminopyridine (DMAP). After a typical work-up by extraction, the residue can be purified by medium pressure liquid chromatography (MPLC) (0% to 40% ethyl acetate in hexanes) to yield the intermediate compound as amorphous solid.

In a second step, the intermediate obtained in the first reaction, can react with methanol (MeOH). The residue can be purified by MPLC (50% ethyl acetate in hexanes then 5% 7N ammonia/methanol/dichloromethane) to yield the desired compound as a solid.

It is to be understood that both the foregoing general description and the following detailed description are exemplary and explanatory only and are not restrictive of the invention claimed. As used herein, the use of the singular includes the plural unless specifically stated otherwise.

The present invention includes all pharmaceutically acceptable isotopically enriched compounds. Any compound of the invention may contain one or more isotopic atoms enriched or different than the natural ratio such as deuterium $^2H$ (or D) in place of protium $^1H$ (or H) or use of $^{13}C$ enriched material in place of $^{12}C$ and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

The IUPAC names of the compounds mentioned in the examples were generated with ACD version 8.0.

Unless specified otherwise in the examples, characterization of the compounds is performed according to the following methods:

NMR spectra are recorded on 300 MHz Varian and acquired at room temperature. Chemical shifts are given in ppm referenced either to internal TMS or to the residual solvent signal.

All the reagents, solvents, catalysts for which the synthesis is not described are purchased from chemical vendors such as Sigma Aldrich, Fluka, Lancaster, however some known reaction intermediates, for which the CAS registry number is mentioned, were prepared in-house following known procedures.

Usually the compounds of the invention were purified by flash column chromatography.

The following abbreviations are used in the examples:

| | |
|---|---|
| DCM | dichloromethane |
| MeOH | methanol |
| CD$_3$OD | deuterated methanol |
| NH$_3$ | ammonia |
| Na$_2$SO$_4$ | sodium sulfate |
| DMF | N,N-dimethylformamide |
| MgSO$_4$ | magnesium sulfate |
| EtOAc | ethylacetate |
| i-PrOH | iso-propanol |
| CDCl$_3$ | deuterated chloroform |
| MPLC | medium pressure liquid chromatography |
| DMF | dimethylformamide |
| TEA | triethylamine |
| THF | tertahydrofuran |
| DMAP | 4-dimethylaminopyridine |
| RT | room temperature |
| Boc-L-Valine | N-(tert-Butoxycarbonyl)-L-valine |
| Boc-Glycine | N-(tert-Butoxycarbonyl)glycine |
| Boc-L-Phenylalanine | N-(tert-Butoxycarbonyl)-L-phenylalanine |
| HCl | hydrochloric acid |
| H$_2$O | water |
| EDCl | 1-ethyl-3-(3-dimethylaminopropyl)carbodiimide |
| NaHCO$_3$ | sodium bicarbonate |

Example 1

Intermediate 1 iso-Butyric acid 3-[(S)-1-(1-isobutyryl-1H-imidazol-4-yl)-ethyl]-2-methyl-benzyl ester To a solution of (S)-[3-(1-(1H-imidazol-4-yl)ethyl)-2-methylphenyl]methanol (1.34 g, 6.2 mmol) in DMF (8 ml) and THF (50 ml), were added TEA (3.5 ml, 24.8 mmol), DMAP (780 mg, 6.2 mmol) and iso-butyryl chloride (2.18 g, 20.5 mmol). The resulting mixture was stirred at RT for 16 h, quenched with H$_2$O and extracted with ethyl acetate. The combined organic layers were washed with brine, and dried over Na$_2$SO$_4$, and concentrated under reduced pressure. The residue was purified by MPLC (0% to 40% ethyl acetate in hexanes) to yield Intermediate 1 as a solid.

$^1$H-NMR (CD$_3$OD, δ ppm): 1.15 (d, J=7.03 Hz, 6H), 1.26 (d, 6H, J=6.74 Hz), 1.56 (d, J=7.03 Hz, 3H), 2.34 (s, 3H), 2.58 (hept, J=7.03 Hz, 1H), 3.34 (hept, J=7.74 Hz, 1H), 4.42 (q, J=7.03 Hz, 1H), 5.15 (s, 2H), 7.07-7.10 (m, 2H), 7.12-7.15 (m, 1H), 7.31 (s, 1H), 8.35 (s, 1H).

Intermediates 2-6 were prepared in a similar manner to the method described in Example 1 starting with (S)-[3-(1-(1H-imidazol-4-yl)ethyl)-2-methylphenyl]methanol. The acyl chloride used in each case and the results are tabulated below in Table 1.

TABLE 1

| Intermediate number | IUPAC name | Acyl chloride | $^1$NMR (Solvent; δ ppm) |
|---|---|---|---|
| 2 | 2,2-Dimethyl-propionic acid 3-{(S)-1-[1-(2,2-dimethyl-propionyl)-1H-imidazol-4-yl]-ethyl}-2-methyl-benzyl ester | Pivaloyl chloride | (CD$_3$OD): 1.19 (s, 9H), 1.42 (s, 9H), 1.56 (d, J = 7.03 Hz, 3H), 2.34 (s, 3H), 4.42 (q, J = 7.03 Hz, 1H), 5.15 (s, 2H), 7.07-7.10 (m, 2H), 7.12-7.15 (m, 1H), 7.33 (s, 1H), 8.40 (s, 1H). |
| 3 | Acetic acid 3-[(S)-1-(1-acetyl-1H-imidazol-4-yl)-ethyl]-2-methyl-benzyl ester | Acetyl chloride | (CD$_3$OD): 1.55 (d, J = 7.03 Hz, 3H), 2.05 (s, 3H), 2.33 (s, 3H), 2.58 (s, 3H), 4.39 (q, J = 7.03 Hz, 1H), 5.15 (s, 2H), 7.07-7.10 (m, 2H), 7.12-7.15 (m, 1H), 7.30 (s, 1H), 8.29 (s, 1H). |
| 4 | Benzoic acid 3-[(S)-1-(1-benzoyl-1H-imidazol-4-yl)-ethyl]-2-methyl-benzyl ester: | Benzoyl chloride | (CD$_3$OD): 1.58 (d, J = 7.03 Hz, 3H), 2.43 (s, 3H), 4.46 (q, J = 7.03 Hz, 1H), 5.41 (s, 2H), 7.11-7.18 (m, 2H), 7.27-7.35 (m, 2H), 7.42-7.50 (m, 2H), 7.50-7.63 (m, 3H), 7.65-7.71 (m, 1H), 7.79 (d, J = 7.33 Hz, 2H), 8.00 (d, J = 7.33 Hz, 2H), 8/09 (s, 1H). |

TABLE 1-continued

| Intermediate number | IUPAC name | Acyl chloride | $^1$NMR (Solvent; δ ppm) |
|---|---|---|---|
| 5 | 3-Methyl-butyric acid 2-methyl-3-{(S)-1-[1-(3-methyl-butyryl)-1H-imidazol-4-yl]-ethyl}-benzyl ester | Methylbutanoyl chloride | (CD$_3$OD): 0.91 (d, J = 6.44 Hz, 6H), 1.01 (d, J = 6.44 Hz, 6H), 1.54 (d, J = 7.03 Hz, 3H), 2.05 (hept, J = 6.44 Hz, 1H), 2.15-2.25 (m, 3H), 2.33 (s, 3H), 2.81 (d, J = 7.03 Hz, 3H), 4.42 (q, J = 7.03 Hz, 1H), 5.14 (s, 2H), 7.07-7.19 (m, 3H), 7.28 (s, 1H), 8.32 (s, 1H). |
| 6 | 3-Phenyl-propionic acid 2-methyl-3-{(S)-1-[1-(3-phenyl-propionyl)-1H-imidazol-4-yl]-ethyl}-benzyl ester | Phenylpropanoyl chloride | (CD$_3$OD): 1.52 (d, J = 7.03 Hz, 3H), 2.24 (s, 3H), 2.64 (t, J = 7.61 Hz, 2H), 2.90 (t, J = 7.61 Hz, 2H), 3.04 (t, J = 7.61 Hz, 2H), 3.24 (t, J = 7.61 Hz, 2H), 4.34 (q, J = 7.03 Hz, 1H), 5.13 (s, 2H), 7.08-7.248 (m, 14H), 8.25 (s, 1H). |

Example 2

Compound 1 iso-Butyric acid 3-[(S)-1-(1H-imadazol-4-yl)-ethyl]-2-methyl-benzyl ester

Intermediate 1 was dissolved in MeOH (50 ml) and the mixture was stirred at RT for 24 h and then concentrated under reduced pressure. The residue was purified by MPLC (50% ethyl acetate in hexanes then 5% 7N NH$_3$/MeOH/DCM) to yield Compound 1 as a solid.

$^1$H-NMR (CD$_3$OD; δ ppm): 1.15 (d, J=7.03 Hz, 6H), 1.54 (d, J=7.03 Hz, 3H), 2.33 (s, 3H), 2.56 (hept, J=7.03 Hz, 1H), 4.42 (q, J=7.03 Hz, 1H), 5.15 (s, 2H), 6.70 (s, 1H), 7.07-7.10 (m, 2H), 7.12-7.15 (m, 1H), 7.55 (s, 1H).

Compounds 2-6 and of the invention were prepared according to the procedure described in Example 2, by reacting the corresponding intermediate with methanol. The results are tabulated below in Table 2.

TABLE 2

| Comp. No. | IUPAC name | Inter. No. | $^1$NMR (Solvent, δ ppm) |
|---|---|---|---|
| 2 | 2,2-Dimethyl-propionic acid 3-[(S)-1-(1H-imidazol-4-yl)-ethyl]-2-methyl-benzyl ester  | 2 | (CD$_3$OD): 1.19 (s, 9H), 1.54 (d, J = 7.03 Hz, 3H), 2.33 (s, 3H), 4.42 (q, J = 7.03 Hz, 1H), 5.13 (s, 2H), 6.70 (s, 1H), 7.07-7.10 (m, 2H), 7.12-7.15 (m, 1H), 7.55 (s, 1H). |

TABLE 2-continued

| Comp. No. | IUPAC name | Inter. No. | $^1$NMR (Solvent, δ ppm) |
|---|---|---|---|
| 3 | Acetic acid 3-[(S)-1-(1H-imidazol-4-yl)-ethyl]-2-methyl-benzyl Ester | 3 | (CD$_3$OD): 1.54 (d, J = 7.03 Hz, 3H), 2.04 (s, 3H), 2.33 (s, 3H), 4.42 (q, J = 7.03 Hz, 1H), 5.13 (s, 2H), 6.70 (s, 1H), 7.07-7.10 (m, 2H), 7.12-7.15 (m, 1H), 7.55 (s, 1H). |
| 4 | Benzoic acid 3-[(S)-1-(1H-imidazol-4-yl)-ethyl]-2-methyl-benzyl Ester | 4 | (CD$_3$OD): 1.54 (d, J = 7.03 Hz, 3H), 2.31 (s, 3H), 4.42 (q, J = 7.03 Hz, 1H), 5.13 (s, 2H), 6.70 (s, 1H), 7.07-7.15 (m, 2H), 7.25-7.28 (m, 1H), 7.54-7.47 (m, 2H), 7.55-7.60 (m, 2H), 8.0 (d, J = 7.33 Hz, 2H). |
| 5 | 3-Methyl-butyric acid 3-[(S)-1-(1H-imidazol-4-yl)-ethyl]-2-methyl-benzyl Ester | 5 | (CD$_3$OD): 0.93 (d, J = 7.03 Hz, 6H), 1.54 (d, J = 7.03 Hz, 3H), 2.07 (hept, J = 7.03 Hz, 1H), 2.21 (d, J = 7.03 Hz, 2H), 2.33 (s, 3H), 4.42 (q, J = 7.03 Hz, 1H), 5.15 (s, 2H), 6.70 (s, 1H), 7.07-7.10 (m, 2H), 7.12-7.15 (m, 1H), 7.55 (s, 1H). |
| 6 | 3-Phenyl-propionic acid 3-[(S)-1-(1H-imidazol-4-yl)-ethyl]-2-methyl-benzyl Ester | 6 | (CD$_3$OD): 1.54 (d, J = 7.03 Hz, 3H), 2.23 (s, 3H), 2.65 (t, J = 7.61 Hz, 2H), 2.91 (t, J = 7.61 Hz, 2H), 4.40 (q, J = 7.03 Hz, 1H), 5.13 (s, 2H), 6.70 (s, 1H), 7.08-7.24 (m, 8H), 7.55 (s, 1H). |

Example 3

Intermediate 7

2-tert-Butoxycarbonylamino-3-methyl-butyric acid 3-{(S)-1-[1-(2-tert-butoxy carbonylamino-3-methyl-butyryl)-1H-imidazol-4-yl]-ethyl}-2-methyl-benzyl ester To a solution of (S)-[3-(1-(1H-imidazol-4-yl)ethyl)-2-methylphenyl]methanol (216 mg, 1.0 mmol) in DMF (2 ml) and THF (12 ml) were added EDCI (671 mg, 3.5 mmol), DMAP (427 mg, 3.5 mmol) and Boc-L-Valine (651 mg, 3.0 mmol). The mixture was stirred at RT for 16 h, quenched with H$_2$O and extracted with ethyl acetate. The combined organic layers were washed with H$_2$O, brine, and dried over Na$_2$SO$_4$, and concentrated under reduced pressure. The residue was purified by a column chromatography (30% ethyl acetate in hexanes) to yield Intermediate 7 as white solid.

$^1$H-NMR (CD$_3$OD; δ ppm): 0.85-1.01 (m, 12H), 1.20-1.48 (m, 18H), 1.56 (d, J=7.03 Hz, 3H), 2.01-2.20 (m, 2H), 2.35 (s, 3H), 4.03 (m, 1H), 4.42 (q, J=7.03 Hz, 1H), 4.60-4.65 (m, 1H), 5.15-5.29 (m, 2H), 7.10-7.20 (m, 2H), 7.20-7.25 (m, 1H), 7.33 (s, 1H), 8.44 (s, 1H).

Example 4

Intermediate 8

2-tert-Butoxycarbonylamino-3-methyl-butyric acid 3-[(S)-1-(1H-imidazol-4-yl)-ethyl]-2-methyl-benzyl ester

The title compound was prepared from Intermediate 7 (600 mg, 0.98 mmol) in 30 ml of MeOH according to the procedure described in Example 2.

$^1$H-NMR (CD$_3$OD; δ ppm): 0.85-0.95 (m, 6H), 1.42 (m, 9H), 1.54 (d, J=7.03 Hz, 3H), 2.05 (m, 1H), 2.33 (s, 3H), 4.00

(d, J=6.15 Hz, 1H), 4.40 (q, J=7.03 Hz, 1H), 5.15-5.28 (m, 2H), 6.67 (s, 1H), 7.10-7.20 (m, 2H), 7.20-7.25 (m, 1H), 7.55 (s, 1H).

Example 5

Compound 7

2-Amino-3-methyl-butyric acid 3-
[(S)-1-(1H-imidazol-4-yl)-ethyl]-
2-methyl-benzyl ester To Intermediate 8 (390 mg, 0.94 mmol) was added 4N HCl in dioxane (8 ml). The resulting solution was stirred at RT for 4 hrs, then quenched with $H_2O$, neutralized with aqueous saturated $NaHCO_3$ and extracted with 25% isopropyl alcohol in chloroform. The combined organic layers were dried over $Na_2SO_4$, and concentrated under reduced pressure. The residue was purified by a column chromatography (5% 7N $NH_3$/MeOH in DCM) to yield Compound 7 as white solid.

$^1$H-NMR (CD$_3$OD; δ ppm): 0.85 (d, J=6.74 Hz, 3H), 0.91 (d, J=6.74 Hz, 3H), 1.54 (d, J=7.03 Hz, 3H), 1.96 (hept, J=6.74 Hz, 1H), 2.33 (s, 3H), 3.28 (d, J=6.74 Hz, 2H), 4.42 (q, J=7.03 Hz, 1H), 5.20-5.25 (m, 2H), 6.67 (s, 1H), 7.10-7.12 (m, 2H), 7.13-7.20 (m, 1H), 7.55 (s, 1H).

Example 6

Intermediate 9

2-(2-tert-Butoxycarbonylamino-3-methyl-butyry-
lamino)-3-methyl-butyric acid 3-{(S)-1-[1-(2-tert-
butoxycarbonylamino-3-methyl-butyryl)-1H-imida-
zol-4-yl]-ethyl}-2-methyl-benzyl ester The title compound was prepared from Compound 7 (490 mg, 1.55 mmol), Boc-L-Valine (1.01 g, 4.67 mmol), EDCI (1.04 g, 5.42 mmol) and DMAP (671 mg, 5.5 mmol) according to the procedure described in Example 3.

$^1$H-NMR (CD$_3$OD; δ ppm): 0.85-0.92 (m, 12H), 1.43 (s, 9H), 1.55 (d, J=7.03 Hz, 3H), 1.97 (m, 1H), 2.14 (hept, J=6.60 Hz, 1H), 2.35 (s, 3H), 3.88 (d, J=7.30 Hz, 1H), 4.35 (d, J=6.90 Hz, 1H), 4.42 (, d, J=7.03 Hz, 1H), 5.18-5.25 (m, 2H), 6.67 (s, 1H), 7.10-7.15 (m, 2H), 7/17-7.20 (m, 1H), 7.55 (s, 1H).

Example 7

Intermediate 10

2-(2-tert-Butoxycarbonylamino-3-methyl-butyry-
lamino)-3-methyl-butyric acid 3-[(S)-1-(1H-imida-
zol-4-yl)-ethyl]-2-methyl-benzyl ester The title compound was prepared from Intermediate 9 (750 mg, 1.05 mmol) in 30 ml of MeOH according to the procedure described in Example 2.

$^1$H-NMR (CD$_3$OD; δ ppm): 0.89 (d, d, J=7.03 Hz, 6H), 1.44 (s, 9H), 1.54 (d, J=7.33 Hz, 3H), 2.14 (hept, J=6.74 Hz, 1H), 2.33 (s, 3H), 3.74 (s, 2H), 4.35-4.55 (m, 2H), 5.20 (s, 2H), 6.67 (s, 1H), 7.10-7.17 (m, 2H), 7.19-7.23 (m, 1H), 7.56 (s, 1H).

Example 8

Compound 8

2-(2-Amino-3-methyl-butyrylamino)-3-methyl-butyric acid 3-[(S)-1-(1H-
imidazol-4-yl)-ethyl]-2-methyl-benzyl ester The title compound was prepared from Intermediate 10 (450 mg, 0.87 mmol) in 8 ml of 4N HCl/Dioxane according to the procedure described in Example 5.

$^1$H-NMR (CD$_3$OD; δ ppm): 0.85 (d, J=7.03 Hz, 3H), 0.91 (d, J=6.74 Hz, 3H), 0.92 (d, J=7.3 Hz. 3H), 1.14 (d, J=6.2 Hz, 3H), 1.54 (d, J=7.03 Hz, 3H), 1.94 (hept, J=5.2 Hz, 1H), 2.14 (hept, J=6.2 Hz, 1H), 2.33 (s, 3H), 3.18 (d, J=5.2 Hz, 1H), 4.34 (d, J=6.2 Hz, 1H), 4.42 (q, J=7.03 Hz, 1H), 5.21-5.26 (m, 2H), 6.67 (s, 1H), 7.10-7.15 (m, 2H), 7.18-7.20 (m, 1H), 7.55 (s, 1H).

Example 9

Intermediate 11

2-(2-tert-Butoxycarbonylamino-acetylamino)-3-me-
thyl-butyric acid 3-[(S)-1-(1H-imidazol-4-yl)-ethyl]-
2-methyl-benzyl ester The title compound was prepared from Compound 8 (405 mg, 1.28 mmol), Boc-Glycine (675 mg, 3.86 mmol), EDCI (859 mg, 4.48 mmol) and DMAP (547 mg, 4.48 mmol) according to the procedure described in Example 3. The title compound was purified by column chromatography using 5% 7N $NH_3$/MeOH in DCM.

$^1$H-NMR (CD$_3$OD; δ ppm): 0.89 (d, J=6.74 Hz, 3H), 0.91 (d, J=6.74 Hz, 3H), 1.55 (d, J=7.30 Hz, 3H), 2.14 (hept, J=6.74 Hz, 1H), 2.33 (s, 3H), 4.37 (d, J=5.90 Hz, 1H), 4.42 (q, J=7.03 Hz, 1H), 5.20-5.25 (m, 2H), 6.67 (s, 1H), 7.10-7.12 (m, 2H), 7.13-7.20 (m, 1H), 7.55 (s, 1H).

Example 10

Compound 9

2-(2-Amino-acetylamino)-3-methyl-butyric acid 3-
[(S)-1-(1H-imidazol-4-yl)-ethyl]-
2-methyl-benzyl ester The title compound was prepared from Intermediate 11 (320 mg, 0.68 mmol) with 10 ml of 4N HCl/Dioxane according the procedure described in Example 5.

$^1$H-NMR (CD$_3$OD; δ ppm): 0.89 (d, J=6.74 Hz, 3H), 0.91 (d, J=6.74 Hz, 3H), 2.14 (hept, J=6.74 Hz, 1H), 2.33 (s, 3H), 4.37 (d, J=5.90 Hz, 1H), 4.42 (q, J=7.03 Hz, 1H), 5.20-5.25 (m, 2H), 6.67 (s, 1H), 7.10-7.12 (m, 2H), 7.13-7.20 (m, 1H), 7.55 (s, 1H).

Example 11

Intermediate 12

2-tert-Butoxycarbonylamino-3-phenyl-propionic acid 3-[(S)-1-(1H-imidazol-4-yl)-ethyl]-2-methyl-benzyl ester The title compound was prepared from (S)-[3-(1-(1H-imidazol-4-yl)ethyl)-2-methylphenyl]methanol (216 mg, 1.0 mmol), Boc-L-Phenylalanine (795 mg, 3.0 mmol), EDCI (671 mg, 3.5 mmol) and DMAP (427 mg, 3.5 mmol) according to the procedure described in Example 3. Intermediate 12 was purified by a column chromatography using 35-100% ethyl acetate in hexane.

$^1$H-NMR (CD$_3$OD; δ ppm): 1.36 (s, 9H), 1.55 (d, J=7.03 Hz, 3H), 2.28 (s, 3H), 2.85-2.95 (m, 1H), 3.05-3.11 (m, 1H), 4.38 (m, 1H), 4.40 (q, J=7.03 Hz, 1H), 5.17 (s, 2H), 6.69 (s, 1H), 7.08-7.24 (m, 8H), 7.55 (s, 1H).

Example 12

Compound 10

2-Amino-3-phenyl-propionic acid 3-
[(S)-1-(1H-imidazol-4-yl)-ethyl]-
2-methyl-benzyl ester The title compound was prepared from Intermediate 12 (240 mg, 0.52 mmol) with 8 ml of 4N HCl/Dioxane according to the procedure described in Example 5.

$^1$H-NMR (CD$_3$OD; δ ppm): 1.54 (d, J=7.03 Hz, 3H), 2.26 (s, 3H), 2.90-3.00 (m, 2H), 3.73 (t, J=6.40 Hz, 1H), 4.40 (q, J=7.03 Hz, 1H), 5.13-5.18 (m, 2H), 6.68 (s, 1H), 7.08-7.12 (m, 5H), 7.13-7.22 (m, 3H), 7.55 (s, 1H).

Example 13

In Vitro Human Skin Permeability Assay

Human, ex vivo, trunk skin was cut into multiple smaller sections large enough to fit on nominal 2 cm$^2$ static Franz diffusion cells. The dermal receptor compartment was filled to capacity with receptor solution consisting of 0.1× phosphate buffered solution with 0.1% Oleth-20, and the epidermal chamber (chimney) is left open to ambient laboratory environment. The cells were placed in a diffusion apparatus in which the receptor solution in contact with the underside of the dermis was stirred magnetically at ~600 RPM and its temperature maintained to achieve a skin surface temperature of 32.0±1.0° C.

To assure the integrity of each skin section, its permeability to tritiated water was determined before application of the test products. Skin specimens in which absorption of $^3$H$_2$O was less than 1.56 μL-equ/cm$^2$ were considered acceptable. [3-(1-(1H-imidazol-4-yl)ethyl)-2-methylphenyl]methanol, Compound 2 (2,2-Dimethyl-propionic acid 3-[(S)-1-(1H-imidazol-4-yl)-ethyl]-2-methyl-benzyl ester) and Compound 1 (iso-Butyric acid 3-[(S)-1-(1H-imidazol-4-yl)-ethyl]-2-methyl-benzyl ester) were applied separately to three (3) replicate sections of the same donor skin for each donor, evaluating three (3) donors for the designated dose duration. A dose of 5 mg formulation/cm$^2$/skin section was evenly dispersed and rubbed into the skin surface using a glass rod.

At designated time points and at the end of the study dose duration, the receptor solution was removed in its entirety, and a predetermined volume aliquot saved for subsequent analysis. After the last receptor sample was collected, the donor compartment (chimney) was removed, and the surface of the skin was cleansed twice to collect any un-absorbed formulation from the skin surface. Following the surface cleanse, the skin was tape stripped to remove the stratum corneum. The tape strips were extracted overnight in acetonitrile and analyzed for content of the compound of interest. The skin was then removed from the diffusion cell, split into epidermis and dermis, and each skin sample extracted overnight in 50%:50% (v/v) ethanol/water or 50%:50% (v/v) methanol water for epidermis and dermis, respectively. The skin section samples were analyzed for content of [3-(1-(1H-imidazol-4-yl)ethyl)-2-methylphenyl]methanol, Compound 2 and Compound 1. All samples were stored at ~−20° C. (±15° C.) pending analysis. Quantitation of [3-(1-(1H-imidazol-4-yl)ethyl)-2-methylphenyl]methanol, Compound 2, and Compound 1 were analyzed by liquid chromatography with tandem mass spectrometry (PLC/MS).

Replicates within donors were averaged and the standard deviation calculated for each key parameter. Within donor averages were then collated and the across donor population mean with standard error of the mean calculated.

Figure 1:
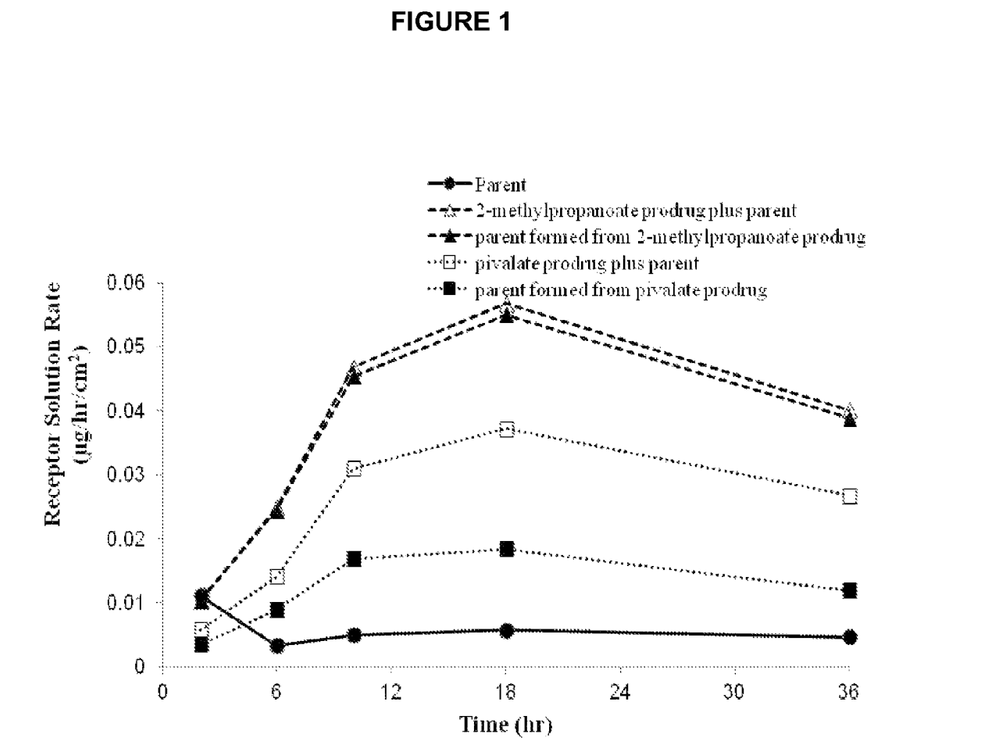
FIG. 1 shows the rate of percutaneous absorption as the flux of [3-(1-(1H-imidazol-4-yl)ethyl)-2-methylphenyl]methanol, Compound 2, pivalate derivative prodrug and Compound 1,2-methylpropanoate derivative prodrug.

FIG. 1 shows the rate of percutaneous absorption as the flux of [3-(1-(1H-imidazol-4-yl)ethyl)-2-methylphenyl]methanol (closed circles, solid line), Compound 2, pivalate derivative prodrug (open squares, dotted line includes parent drug), and Compound 1,2-methylpropanoate derivative prodrug (open triangles and dashed line includes parent drug) that appears in the receptor solution under the skin after a 0.18%, 0.65% and 0.55% (w/w) dose, respectively. The flux of parent drug [3-(1-(1H-imidazol-4-yl)ethyl)-2-methylphenyl]methanol formed after dosing Compound 2, pivalate derivative prodrug (closed squares, dotted line) and Compound 1, 2-methylpropanoate derivative prodrug (closed triangles and dashed line) on human trunk skin are plotted.

Figure 2:
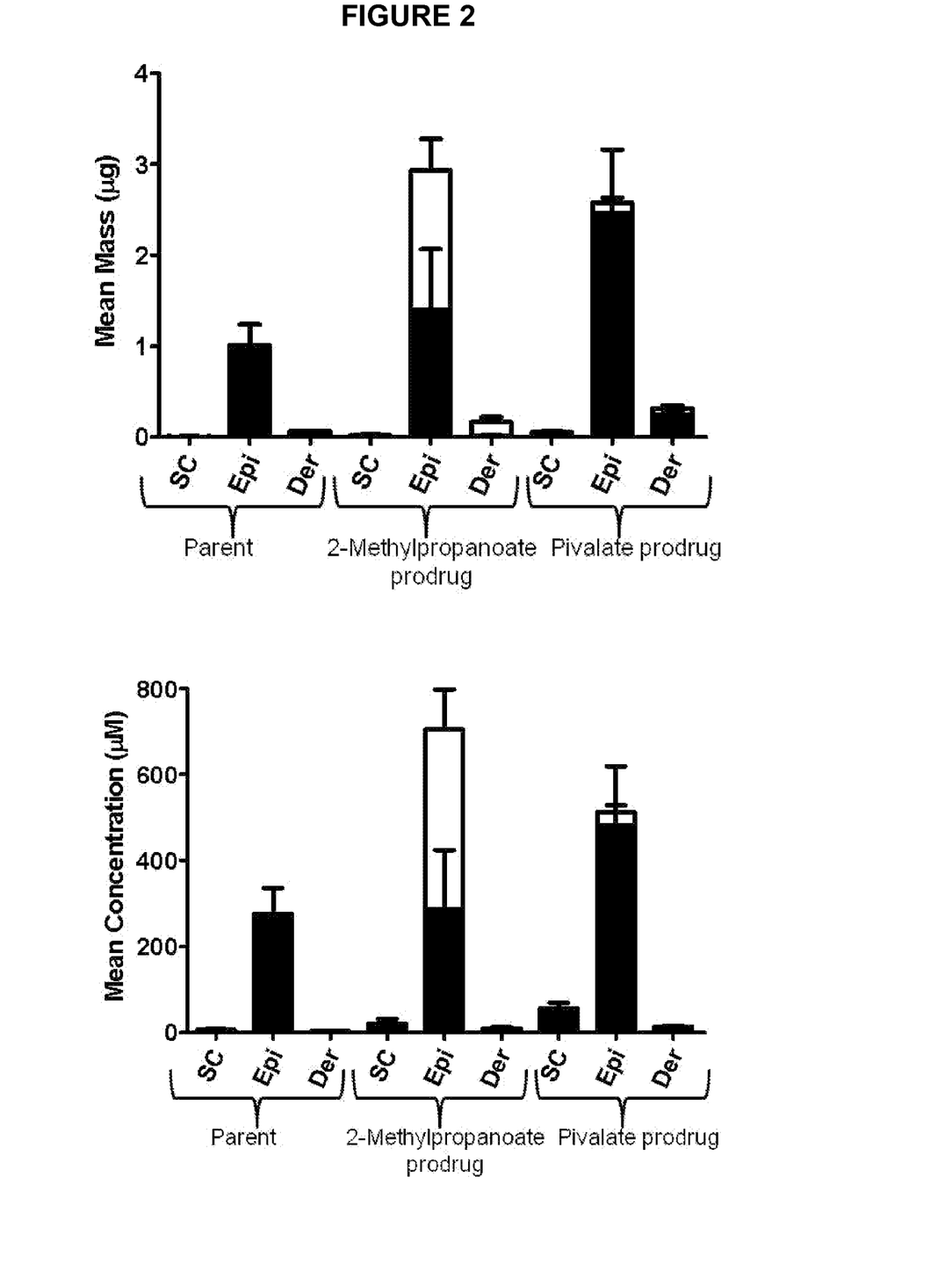
FIG. 2 shows the distribution of [3-(1-(1H-imidazol-4-yl)ethyl)-2-methylphenyl]methanol, Compound 2, pivalate derivative prodrug and Compound 1, 2-methylpropanoate derivative prodrug in each skin layer.

FIG. 2 shows the distribution of [3-(1-(1H-imidazol-4-yl) ethyl)-2-methylphenyl]methanol, Compound 2, pivalate derivative prodrug (open bars represent formed parent), and Compound 1,2-methylpropanoate derivative prodrug (open bars represent formed parent) in each skin layer following a 48 hour dose exposure of a 0.18%, 0.65% and 0.55% (w/w) dose, respectively to ex vivo human trunk skin as a mass recovered.

The data indicate that Compound 2, pivalate derivative and Compound 1, 2-methylpropanoate derivative, penetrate into and through ex vivo human trunk skin using the in vitro Franz diffusion cell.

What is claimed is:
1. A method for treating rosacea in a subject in need of such treatment, which comprises administering a therapeutically effective amount of a composition comprising a compound having Formula I, its individual enantiomers, its individual diastereoisomers, its individual isomers, its individual tautomers or a pharmaceutically acceptable salt thereof, Formula I wherein
$R^1$ is H or optionally substituted $C_{1-3}$ alkyl;
$R^2$ is H or optionally substituted $C_{1-3}$ alkyl;
$R^3$ is H, optionally substituted $C_{1-10}$ alkyl, optionally substituted heterocycle or optionally substituted aryl; and
R is optionally substituted $C_{1-10}$ alkyl, optionally substituted heterocycle or optionally substituted aryl.

2. A method according to claim 1 wherein the compound is of Formula II, its individual diastereoisomers, its individual isomers, its individual tautomers or a pharmaceutically acceptable salt thereof, Formula II wherein
$R^1$ is H or optionally substituted $C_{1-3}$ alkyl;
$R^2$ is H or optionally substituted $C_{1-3}$ alkyl;
$R^3$ is H, optionally substituted $C_{1-10}$ alkyl, optionally substituted heterocycle or optionally substituted aryl; and
R is optionally substituted $C_{1-10}$ alkyl, optionally substituted heterocycle or optionally substituted aryl.

3. A method according to claim 1 wherein the compound is of Formula III, its individual diastereoisomers, its individual isomers, its individual tautomers or a pharmaceutically acceptable salt thereof, Formula III wherein
$R^1$ is H or $C_{1-3}$ alkyl;
$R^2$ is H or optionally substituted $C_{1-3}$ alkyl;
$R^3$ is H, optionally substituted $C_{1-10}$ alkyl, optionally substituted heterocycle or optionally substituted aryl; and
R is optionally substituted $C_{1-10}$ alkyl, optionally substituted heterocycle or optionally substituted aryl.

4. A method according to claim 2, wherein $R^1$ is optionally substituted $C_{1-3}$ alkyl, $R^2$ is optionally substituted $C_{1-3}$ alkyl $R^3$ is H and R is optionally substituted $C_{1-10}$ alkyl.

5. A method according to claim 2, wherein $R^1$ is methyl, $R^2$ is methyl, $R^3$ is H and R is optionally substituted $C_{1-4}$ alkyl.

6. A method according to claim 2, wherein the compound is selected from:
iso-Butyric acid 3-[(S)-1-(1H-imidazol-4-yl)ethyl]-2-methyl-benzyl ester;
2,2-Dimethyl-propionic acid 3-[(S)-1-(1H-imidazol-4-yl)ethyl]-2-methyl-benzyl ester;
Acetic acid 3-[(S)-1-(1H-imidazol-4-yl)-ethyl]-2-methyl-benzyl ester;
Benzoic acid 3-[(S)-1-(1H-imidazol-4-yl)ethyl]-2-methyl-benzyl ester;
3-Methyl-butyric acid 3-[(S)-1-(1H-imidazol-4-yl)ethyl]-2-methyl-benzyl ester;
3-Phenyl-propionic acid 3-[(S)-1-(1H-imidazol-4-yl)ethyl]-2-methyl-benzyl ester;
2-Amino-3-methyl-butyric acid 3-[(S)-1-(1H-imidazol-4-yl)ethyl]-2-methyl-benzyl ester;
2-(2-Amino-3-methyl-butyrylamino)-3-methyl-butyric acid 3-[(S)-1-(1H-imidazol-4-yl)-ethyl]-2-methyl-benzyl ester;
2-(2-Amino-acetylamino)-3-methyl-butyric acid 3-[(S)-1-(1H-imidazol-4-yl)-ethyl]-2-methyl-benzyl ester; and
2-Amino-3-phenyl-propionic acid 3-[(S)-1-(1H-imidazol-4-yl)-ethyl]-2-methyl-benzyl ester.

7. A method according to claim 2, wherein the compound is selected from:
iso-Butyric acid 3-[(S)-1-(1-iso-butyryl-1H-imidazol-4-yl)-ethyl]-2-methyl-benzyl ester;
2,2-Dimethyl-propionic acid 3-{(S)-1-[1-(2,2-dimethyl-propionyl)-1H-imidazol-4-yl]-ethyl}-2-methyl-benzyl ester;
Acetic acid 3-[(S)-1-(1-acetyl-1H-imidazol-4-yl)ethyl]-2-methyl-benzyl ester;
Benzoic acid 3-[(S)-1-(1-benzoyl-1H-imidazol-4-yl)ethyl]-2-methyl-benzyl ester;
3-Methyl-butyric acid 2-methyl-3-{(S)-1-[1-(3-methyl-butyryl)-1H-imidazol-4-yl]-ethyl}-benzyl ester;
Phenyl-propionic acid 2-methyl-3-{(S)-1-[1-(3-phenyl-propionyl)-1H-imidazol-4-yl]-ethyl}-benzyl ester;
2-tert-Butoxycarbonylamino-3-methyl-butyric acid 3-{(S)-1-[1-(2-tert-butoxy carbonylamino-3-methyl-butyryl)-1H-imidazol-4-yl]ethyl}-2-methyl-benzyl ester;
2-tert-Butoxycarbonylamino-3-methyl-butyric acid 3-[(S)-1-(1H-imidazol-4-yl)-ethyl]-2-methyl-benzyl ester;
2-(2-tert-Butoxycarbonylamino-3-methyl-butyrylamino)-3-methyl-butyric acid 3-{(S)-1-[1-(2-tert-butoxycarbonylamino-3-methyl-butyryl)-1H-imidazol-4-yl]ethyl}-2-methyl-benzyl ester;
2-(2-tert-Butoxycarbonylamino-3-methyl-butyrylamino)-3-methyl-butyric acid 3-[(S)-1-(1H-imidazol-4-yl)-ethyl]-2-methyl-benzyl ester;
2-(2-tert-Butoxycarbonylamino-acetylamino)-3-methyl-butyric acid 3-[(S)-1-(1H-imidazol-4-yl)-ethyl]-2-methyl-benzyl ester; and
2-tert-Butoxycarbonylamino-3-phenyl-propionic acid 3-[(S)-1-(1H-imidazol-4-yl)-ethyl]-2-methyl-benzyl ester.

* * * * *

UNITED STATES PATENT AND TRADEMARK OFFICE
CERTIFICATE OF CORRECTION

| | |
|---|---|
| PATENT NO. | : 8,492,422 B2 |
| APPLICATION NO. | : 13/233665 |
| DATED | : July 23, 2013 |
| INVENTOR(S) | : Mohammed I. Dibas et al. |

It is certified that error appears in the above-identified patent and that said Letters Patent is hereby corrected as shown below:

On the Title page, in item (56), under "OTHER PUBLICATIONS", in column 2, line 10, delete "Chemica" and insert -- Chimica --, therefor.

In the Specification

In column 5, line 8, delete "and or" and insert -- and/or --, therefor.

In column 5, line 32, delete "and or" and insert -- and/or --, therefor.

In column 5, line 54, delete "and or" and insert -- and/or --, therefor.

In column 7, line 36, delete "tertracyclines" and insert -- tetracyclines --, therefor.

In column 7, line 47, delete "tertracyclines" and insert -- tetracyclines --, therefor.

In column 7, line 48, delete "phytoshingosine," and insert -- Phytosphingosine, --, therefor.

In column 7, line 64, delete "tertracyclines" and insert -- tetracyclines --, therefor.

In column 8, line 15, delete "tertracyclines" and insert -- tetracyclines --, therefor.

In column 8, line 46, delete "trialklysilyl" and insert -- trialkylsilyl --, therefor.

In column 10, line 45, delete "isooxazolyl," and insert -- isoxazolyl, --, therefor.

In column 11, lines 38-39, delete "yl)ethyl]" and insert -- yl)-ethyl] --, therefor.

In column 11, line 40, delete "yl)ethyl]" and insert -- yl)-ethyl] --, therefor.

In column 12, line 4, delete "butoxy carbonylamino" and insert -- butoxycarbonylamino --, therefor.

In column 12, line 45, delete "palmoic" and insert -- pamoic --, therefor.

In column 12, lines 46-47, delete "napthalenedisulfonic," and insert -- naphthalenedisulfonic, --, therefor.

In column 12, line 50, delete "Stahal" and insert -- Stahl --, therefor.

In column 12, line 51, delete "Chemica" and insert -- Chimica --, therefor.

In column 14, line 10, after "also" delete "the".

In column 14, line 66, delete "and or" and insert -- and/or --, therefor.

Signed and Sealed this
Twenty-second Day of October, 2013

Teresa Stanek Rea
*Deputy Director of the United States Patent and Trademark Office*

CERTIFICATE OF CORRECTION (continued)

U.S. Pat. No. 8,492,422 B2

In column 21, line 54, delete "butoxy carbonylamino" and insert -- butoxycarbonylamino --, therefor.

In column 23, line 49, delete "(,d," and insert -- (d, --, therefor.

In column 23, line 50, delete "7/17-" and insert -- 7.17- --, therefor.

In the Claims

In column 28, line 3, in claim 4, delete "alkyl" and insert -- alkyl, --, therefor.

In column 28, line 8, in claim 6, delete "yl)ethyl]" and insert -- yl)-ethyl] --, therefor.

In column 28, lines 10-11, in claim 6, delete "yl)ethyl]" and insert -- yl)-ethyl] --, therefor.

In column 28, line 15, in claim 6, delete "yl)ethyl]" and insert -- yl)-ethyl] --, therefor.

In column 28, line 17, in claim 6, delete "yl)ethyl]" and insert -- yl)-ethyl] --, therefor.

In column 28, lines 19-20, in claim 6, delete "yl)ethyl]" and insert -- yl)-ethyl] --, therefor.

In column 28, line 22, in claim 6, delete "yl)ethyl]" and insert -- yl)-ethyl] --, therefor.

In column 28, line 38, in claim 7, delete "yl)ethyl]" and insert -- yl)-ethyl] --, therefor.

In column 28, lines 40-41, in claim 7, delete "yl)ethyl]" and insert -- yl)-ethyl] --, therefor.

In column 28, line 47, in claim 7, delete "butoxy carbonylamino" and insert -- butoxycarbonylamino --, therefor.

In column 28, line 48, in claim 7, delete "yl)ethyl}" and insert -- yl)-ethyl} --, therefor.